United States Patent [19]

Weinberg et al.

[11] Patent Number: 4,740,463
[45] Date of Patent: Apr. 26, 1988

[54] METHODS AND ARTIFICIAL GENES FOR ANTAGONIZING THE FUNCTION OF AN ONCOGENE

[75] Inventors: Robert A. Weinberg, Brookline, Mass.; Cornelia I. Bargmann, Athens, Ga.; David F. Stern, Cambridge, Mass.

[73] Assignee: Massachusetts Institute of Technology, Boston, Mass.

[21] Appl. No.: 599,936

[22] Filed: Apr. 13, 1984

[51] Int. Cl.$^4$ .................. C12N 15/00; C07H 21/04; C12P 19/34
[52] U.S. Cl. ................. 435/172.3; 435/320; 435/91; 536/27
[58] Field of Search .................. 435/172.3, 235, 317, 435/91, 320; 536/27-29

[56] References Cited

U.S. PATENT DOCUMENTS 4,405,712  9/1983  Varde Woude et al. ........... 435/235

OTHER PUBLICATIONS

Chemical Abstracts, vol. 93, Abstract No. 3727y, 1980.
Chemical Abstracts, vol. 99, Abstract No. 116988b, 1983.
Chemical Abstracts, vol. 93, Abstract No. 234901s, 1980.
McCoy M. S., C. I. Bargmann and R. A. Weinberg, Human Colon Carcinoma Ki-ras2 Oncogene and Its Corresponding Proto-Oncogene, *Molecular and Cellular Biology*, 4:1577–1582, (1984).
Mizuno, T., M. Y. Chore and M. Inouye, A Unique Mechanism Regulating Gene Expression: Translational Inhibition by a Complementary RNA transcript (micRNA), *Proceedings of the National Academy of Sciences*, USA, 81: 1966–1970, (1984).
Izant, J. G. and H. Weintraub, Inhibition of Thymidine Kinase Gene Expression by Anti-sense RNA: a Molecular Approach to Genetic Analysis, Cell, 36:1007–1015, (1984).

*Primary Examiner*—Blondel Hazel
*Attorney, Agent, or Firm*—Hamilton, Brook, Smith & Reynolds

[57] ABSTRACT

A method of antagonizing the effects of an oncogene by constructing an artificial gene which antagonizes the function of the oncogene is described herein. In one embodiment, the artificial gene comprises a transcriptional promoter segment, an inverted oncogene segment, and a polyadenylation segment.

25 Claims, 6 Drawing Sheets

TRIPARTITE CONSTRUCTIONS
(Arrows denote orientation of oncogene.)

METHODS AND ARTIFICIAL GENES FOR ANTAGONIZING THE FUNCTION OF AN ONCOGENE

The Government has rights in this invention pursuant to Grant No. NIH-2-R01-CA17537-09 awarded by the Department of Health & Human Services.

TECHNICAL FIELD

This invention is in the field of molecular biology and relates to oncogenes.

BACKGROUND ART

Although the molecular basis for malignant transformation leading to cancer is not yet fully understood, much information has been developed recently using molecular biology techniques. For example, while it has long been thought that transformation involved the alteration of critical genes, referred to as "oncogenes", such discrete oncogenes have only recently been isolated and shown to cause transformation.

For example, isolated human sequences from the c-K-ras oncogene present in certain human lung tumors have been described. See Nakano, H., Yamamoto, F., Neville, C., Evans, D., Mizuno, T., and Perucho, M., "Isolation of Transforming Sequences of Two Human Lung Carcinomas: Structural and Functional Analysis of the Activated c-K-ras Oncogenes", *Proc. Acad. Sci. USA*, 81, 71–75, January, 1984; Santos, E., Martin-Zanca, M., Reddy, P., Pierotti, M. A., Della Porta, G., Barbacid, M., "Malignant Activation of A K-ras Oncogene and Lung Carcinoma But Not in Normal Tissue of the Same Patient", *Science*, 223, pp. 661–4, Feb. 17, 1984. Additionally, an oncogene isolated from the EJ bladder carcinoma cell line has been found to cause transformation when it was transfected into NIH 3T3 cells. See Shih, C., and Weinberg, R., Cell, 29, 161–9 (1982).

DISCLOSURE OF THE INVENTION

This invention relates to Applicants' discovery of a method for antagonizing the function of an oncogene. In this method, an artificial gene is constructed so that, upon introduction into a cell containing the oncogene, the artificial gene produces an RNA transcript which antagonizes the function of the oncogene. More specifically, the antagonizing gene is constructed to include: (1) a transcriptional promoter segment; (2) an oncogene segment that is inverted with regard to the transcriptional promoter; and (3) a polyadenylation segment.

Transcription of the inverted oncogene segment occurs along the complementary strand of DNA, which is not transcribed in the oncogene itself to produce an RNA transcript capable of antagonizing the function of the oncogene. Thus, the artificially-constructed gene can be introduced into a cell containing an oncogene to antagonize the function of the oncogene.

In a further embodiment of the invention, the function of the oncogene is antagonized and proto-oncogene function is restored to a cell. In this embodiment, a first artificially-constructed gene, as described above, is introduced into cells containing an oncogene to antagonize the function of the oncogene. In addition, a second artificially-constructed gene is introduced into the same cells and the second gene is constructed to restore proto-oncogene function to the cell; its function is not antagonized by the first gene.

By employing this invention, the function of an oncogene can be antagonized in intact cells without the necessity of disrupting the cells' structure. Further, the artificially constructed genes can be designed to be selective for antagonism of a gene of choice within cells, leaving other genes to function normally. Additionally, this invention provides a method by which the function of an oncogene can be antagonized while simultaneously restoring proto-oncogene function to cells containing the oncogene.

BEST MODE FOR CARRYING OUT THE INVENTION

As used herein, the term "oncogene" is used to mean a genetic sequence whose expression within a cell provides a function, including one of several functions, in the steps leading from a normal cell into a tumor cell. Similarly, the term "proto-oncogene" is used herein to mean a genetic sequence, residing in the normal genome of a normal, non-tumor cell, which has the potential, when altered in the appropriate manner, of becoming an oncogene.

The experimental work described herein employed the k-ras oncogene. Additional oncogenes are known to those skilled in the art. These include, for example, the h-ras and n-ras oncogenes which have been implicated in many human tumors. See Tabin et al., *Nature*, 300, p. 143 (1982); and Shimizu et al., PNAS 80, p. 2112 (1983). Additionally, the myc gene has reported to be aberrantly expressed in Burkitt's lymphomas, and n-myc has been reported as being expressed at high levels in neuroblastomas. See Taub et al., PNAS, 79, p. 7837 (1982) and Schwab et al., *Nature*, 305, p. 245 (1983).

HTLV, a human retrovirus, is also believed to contain genes important to tumorigenesis whose function can be antagonized by the methods of this invention. See Wong-Staal et al., *Nature*, 302, p. 626 (1983). Additionally, many oncogenes have been isolated in mammalian and avian retroviruses and are suspected of being important in human tumors. These include src, erb, yes, fes, raf, myb, fos, rel, ski, etc. It is believed that oncogene function of these genes could be antagonized by the methods of this invention.

An additional description of oncogenes is contained in Weinberg, R. A., *Science*, (1984), the teachings of which are hereby incorporated by reference.

Oncogenes may be present in cells because they are introduced by experimental manipulation, such as gene transfer. Alternatively, oncogenes can be introduced into cells by an applied viral vector capable of carrying the oncogene into cells or may be introduced by a naturally occurring virus whose genome carries the oncogene. Additionally, an oncogene may be present in a tumor cell because of mutation occurring in a cell that was ancestral to the tumor cell, the mutation creating an oncogene from a pre-existing normal cellular gene, i.e., proto-oncogene.

Figure 1:
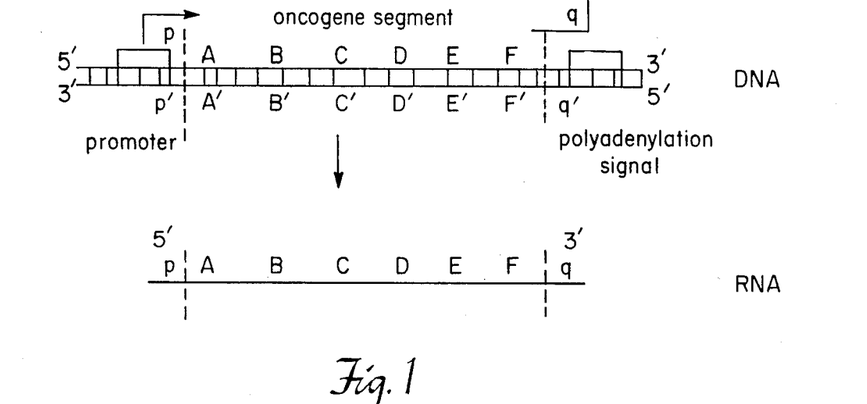
FIG. 1 is a schematic illustration of double-stranded DNA containing an oncogene, and illustrates transcription of the oncogene to produce an RNA transcript.

FIG. 1 illustrates transcription of an oncogene. Therein, an oncogene is illustrated having two strands of DNA complementary to each other, of opposite polarity, that constitute a single DNA molecule. The complementarity is indicated by lines connecting the two strands of DNA. Thus, sequence A is complementary to sequence A' on the opposite strand of DNA, sequence B is complementary to sequence B' on the opposite strand of DNA, and so forth.

Transcription of the DNA molecule directs synthesis of one strand of RNA having sequences complementary to the sequences on the strand of DNA transcribed. Thus, the RNA transcript has sequences A–F which are complementary to the sequence of the transcribed strand A'–F' of DNA. Such an RNA transcript is sometimes referred to as sense RNA.

Figure 2:
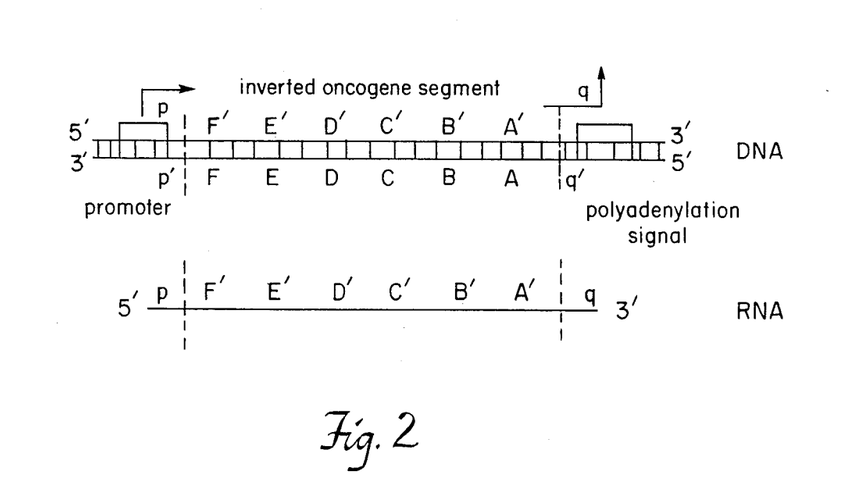
FIG. 2 is a schematic illustration of an artificially-constructed gene capable of antagonizing the function of the oncogene of FIG. 1.

FIG. 2 illustrates the construction of a tripartite gene designed to antagonize the oncogene shown in FIG. 1. The dotted lines indicate where the DNA molecule is cut, employing restriction enzymes, to create the tripartite construction. The two strands of DNA containing the oncogene segment are cleaved and inverted 180° with respect to the promoter and polyadenylation signal. The polarity of the inverted strand is the same as the polarity of the sequence into which it is inserted. Such inversion results in the F-A sequence of DNA being transcribed. As a result, the RNA transcript of the gene illustrated in FIG. 2 is complementary to the F-A sequence.

The promoter serves as a signal conferring expression on the sequences that lie on one side of it. It may be construed as all the signals necessary for successful initiation of transcription in a given cell type, including sequences such as enhancers, TATA boxes, and other signals. Its operation is taken to be strictly polar, leading to transcription of one of the two strands of DNA in a 3' to 5' direction on the DNA, leading to a 5' to 3' formation of an RNA molecule.

The polyadenylation signal may be construed as such signals that provide an accurate and efficient termination of a transcript, whether by cessation of transcription or a post-transcriptional cleavage event. Polyadenylation itself is a post-transcription processing event in which a cleaved RNA has ribose adenosines attached to its 3' end which may confer stability to the RNA or be involved in processing and transport.

Figure 3:
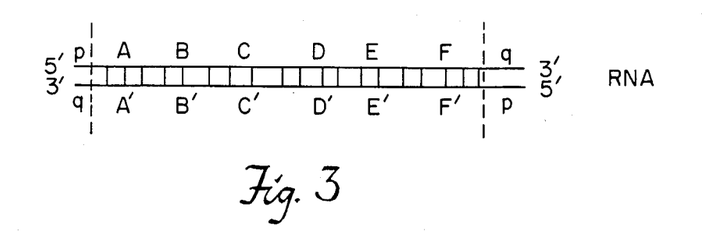
FIG. 3 is a schematic illustration of how the oncogene of FIG. 1 may be antagonized by the artificially-constructed gene of FIG. 2.

FIG. 3 illustrates how the tripartite artificially-constructed gene of FIG. 2 may antagonize the function of the oncogene of FIG. 1. In FIG. 3, an interaction is illustrated that might occur between the RNA transcripts produced by the genes of FIGS. 1 and 2. A complementary interaction involves two strands of opposite polarity to each other, so that the RNA transcript from FIG. 2 is rotated in FIG. 3 so that its 5' end lies to the right rather than the left. The region that was inverted in the tripartite construction of FIG. 2 allows a complementary region to form between the two RNA transcripts. Regions outside the inverted region do not bear a complementary relationship to each other.

The transcriptional promoter can, in principle, be of any origin as long as it specifies a rate of transcription that is compatible with antagonizing the oncogene. To achieve such antagonism, it is desirable to employ a very efficient transcriptional promoter, which eliminates many promoters naturally associated with proto-oncogenes because they are weak promoters. Viral promoters, such as a retrovirus promoter, are potent promoters and therefore function well in the tripartite genes according to this invention. Other sources of potent promoters include cellular genes that are expressed at a high level. These may be genes that are actively and powerfully transcribed in most cell types, such as tubulin genes, or genes that are optimally transcribed only in one or a few cell types, such as globin genes in pre-erythrocytes or muscle actin in myoblasts or myofibrils. Promoters from genes transcribed in only a few cell types would be most useful in the same type of cell.

The promoter segment may be a constitutive promoter or a regulatable promoter. Regulatable promoters provide selectivity to the antagonism of oncogene function. One example of a regulatable promoter is described in: Mayo, K. E., Warren, R. and Palmiter, R. D., "The Mouse Metallothionein-1 Gene Is Transcriptionally Regulated By Cadmium Following Transfection Into Human or Mouse Cells", *Cell*, 29, 99–108 (May 1982), the teaching of which are hereby incorporated by reference. Regulatable promoters may include those that can be regulated externally such as the metallothionein I gene which can be regulated by administration of heavy metals, and those that are regulated internally, such as histone genes that are regulated in the cell cycle.

The oncogene segment which is inverted in the tripartite gene described herein must have a close sequence relationship to the oncogene segment it is constructed to antagonize. Although the precise reason for this is not known, it is likely that this is due to the fact that the two kinds of RNA molecules recognize one another which only happens when they share a close or identical sequence relationship. For this reason, it is often preferred to employ oncogene segments from the same species of origin as the oncogene which is to be antagonized. Despite this, it is believed that oncogene segments from different species of origin than the oncogene to be antagonized will be sufficient in some cases. This is particularly true where the two genes are descended from the same gene carried by a common progenitor organism but have evolved separately during independent evolutions of the two lineages, causing the two genes to have diverged somewhat in consequence; such genes are no longer completely analogous but are closely related and are known as homologs. Indeed, there may be some advantages in some applications to use oncogene segments from species of origin different from the oncogene to be antagonized in such applications.

The polyadenylation segment is employed in the tripartite construction because production of a stable RNA molecule requires that the molecule go through discrete processing or maturation events. These events are facilitated by the presence in a gene of a precise cleavage/processing signal of this nature; the absence of such a signal causes a decreased level of functional, stable RNA molecules in the cytoplasm of the cell. Such a signal could be obtained from a retrovirus, as in this instance, or another virus, or a cellular gene. In each case, it is necessary that the poly A site so provided prove an efficient site of cleavage/termination in the organism and cell in which the antagonism is desired. This can best be determined empirically.

Figure 4:
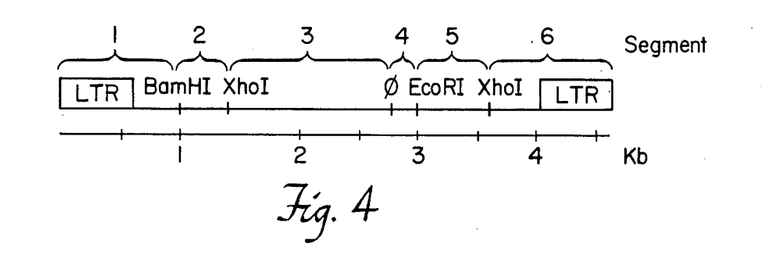
FIG. 4 is a schematic illustration of a six-segment artificially-constructed gene suitable for the insertion of an oncogene segment of DNA according to this invention.
Figure 5:
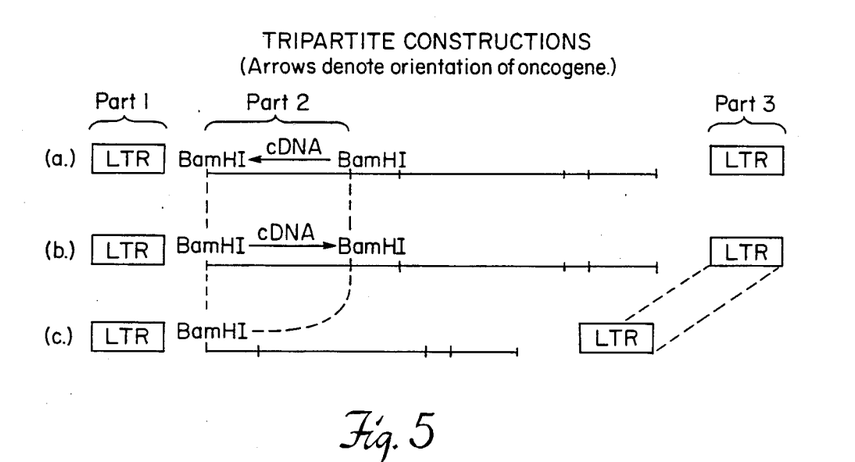
FIG. 5 is a schematic illustration of the insertion of an oncogene segment and an inverted oncogene segment into the six-segment artificially-constructed gene illustrated in FIG. 4.

The construction of a gene capable of antagonizing the function of k-ras oncogene will now be described and is illustrated schematically in FIGS. 4 and 5. This gene is constructed employing a promoter region from the left (5' proximal) end of the Moloney leukemia virus provirus. This 5' proximal proviral segment includes the left (5' proximal) long terminal repeat (LTR) of the provirus; a middle portion containing a cDNA segment of the human cellular cKi-ras2 gene; and a portion that includes the right (3' proximal) LTR of the Moloney leukemia virus provirus, including an associated polyadenylation site.

This particular construct will be referred to as a "6-segment construct" and serves as the basis for constructing tripartite genes as described herein. It can be described as follows, moving from left to right.

Segment 1. This is a derivative of the pZIP plasmid (See Hoffmann et al., *J. Virol* 44: 144–157), whose essential portion is 1 kb (kilobase) long, beginning with 0.6 kb of the left LTR of Moloney murine leukemia virus (MLV) and proceeding another 0.4 kb to the first Pst I site usually encountered in the MLV viral genome (termed the MLV provirus). The Pst I site has been replaced by a Bam HI endonuclease site. Segment 1 contains the transcriptional promoter and, therefore, the first of the 3 elements of a tripartite gene.

Segment 2. This is a 0.4 kb segment derived from the pZIP clone of the MLV provirus, encompassing a "splice-acceptor" site, and originating from the provirus region defined by map units 5.9 to 6.3 and the endonuclease sites BglII and XbaI within the MLV provirus, these two sites having been modified to BamHI and XhoI endonuclease sites, respectively.

Segment 3. This is a 1.4 kb segment that was derived originally from the tn5 neomycin resistance gene was isolated from pBRneo [See Southern and Berg, *J. Mol. Appl. Genet.* 1: 327 (1982)]. This segment was inserted between HindIII and BamHI endonuclease sites at nucleotide positions 29 and 375 within pBR322; in this construction these sites have been replaced by XhoI and a null cleavage site, respectively.

Segment 4. This is a 0.23 kb segment derived from the portion of simian virus 40 (SV40) genome containing the viral origin of replication and mapping from nucleotides 160 to 5154 of the SV40 genome, these two sites representing RII and HindIII endonuclease sites, these sites being replaced by a null cleavage site and an EcoRI cleavage site, respectively, in the construct.

Segment 5. This is a 0.58 kb segment of pBR322 containing the plasmid origin of replication and originating from a ThaI endonuclease-generated fragment extending from nucleotide 2521 to nucleotide 3102 of the pBR322 plasmid. These two ThaI sites being replaced by an EcoRI site on the left and an XhoI site on the right.

Segment 6. This is a 1.05 kb segment deriving from the pZIP plasmid and containing an MLV proviral segment originating at a site at 7.75 map units within the MLV provirus, defined by a HpaI endonuclease site in the naturally occurring provirus and continuing for 0.45 kb until the right LTR of the MLV provirus, and continuing farther for 0.6 kb of the provirus. The naturally occurring Hpa I site has been replaced by an XhoI site in this construct. Thus segment 6 contains the polyadenylation site and therefore constitutes the rightmost segment of a tripartite gene.

The second or middle portion of a tripartite gene is not present in the above 6-segment construction. A site existing between segment 1 and segment 2, and corresponding to a BamHI endonuclease site, exists as an empty cassette into which various versions of the desired middle portion of a tripartite construction can be inserted.

This BamHI cleavage site has been used as a point of entry for the introduction of DNA segments leading to 3 tripartite constructs. These are:

a. A DNA segment homologous to the cKi-ras2 gene of the human genome (See McCoy et al., *Nature*, 302: 79–81, 1983) and being specifically a 1.2 kb DNA segment deriving from reverse transcription of the cKi-ras2 mRNA, being termed therefore a cDNA. This gene was retrieved from a library prepared by Okayama and Berg (See *Mol. Cell. Biol.* 3: 280, 1983). This 1.2 kb cKi-ras2 segment acquired BamHI sites as a consequence of its presence in the Okayama and Berg cloning vector and could be retrieved from said vector by cleavage with endonuclease BamHI. This segment could be introduced into the 6-segment construct at its BamHI site in a fashion such that the promoter of the 6-segment construct will cause synthesis of the anti-sense RNA strand from the cKI-ras2 DNA template.

b. The identical 1.2 kb cKi-ras2 cDNA can be introduced into the same site of the 6-segment construct in the opposite orientation, so that the transcriptional promoter of the 6-segment construct will cause synthesis of "sense" RNA from the cKi-ras2 DNA template.

c. The BamHI site can be left unoccupied, such that no additional DNA is introduced into this site.

These three separately constructed tripartite genes were introduced separately via transfection into NIH3T3 mouse fibroblasts that had previously acquired, via transfection, copies of the oncogene of the human SW480 colon carcinoma cell line. See Murray et al., *Cell*, August, 1981. Cells from each of the three resulting cultures were placed under neomycin selection following transfection and neomycin-resistant colonies were observed and studied in detail. This selection assured outgrowth of only those cells that had acquired a copy or copies of the segment construct and associated inserted segments. Such outgrowth was assured because the 6-segment construct carried a gene ("segment 3" above) conferring resistance to killing by neomycin.

Five out of six colonies carrying the cKi-ras DNA gene inserted in the reverse orientation into the 6-segment construct, thus, carrying an antagonizing gene that served as template for synthesis of "anti-sense RNA," lost their transformed morphology and therefore reverted to normal growth patterns.

Four out of seven colonies that carried the cKi-ras DNA gene inserted in the normal orientation into the 6-segment construct, thus carrying a gene that served as template for synthesis of "sense RNA," retained their transformed morphology and became even "hyper-transformed" in their morphology.

Four out of five colonies that carried no cKi-ras segment inserted into the 6-segment construct showed no effect whatsoever on morphology or growth behavior.

The antagonizing gene can be introduced into cells containing oncogenes by a number of different techniques. One technique is transfection, which can be done by several different methods. One method of transfection involves the addition of DEAE-dextran to increase the uptake of the naked DNA molecules by a recipient cell. See McCutchin, J. H. and Pagano, J. S., *J. Natl. Cancer Inst.*, 41, pp. 351–7 (1968). Another method of transfection is the calcium phosphate precipitation technique which depends upon the addition of Ca++ to a phosphate-containing DNA solution. The resulting precipitate apparently includes DNA in associate with calcium phosphate crystals. These crystals settle onto a cell monolayer, the resulting apposition of crystals and cell surface appears to lead to uptake of the DNA. A small proportion of the DNA taken up becomes expressed in a transfectant, as well as in its clonal descendants. See Graham, F. L. and van der Eb, A. J., *Virology* 52, pp. 456–467 (1973) and Graham, F. L. an van der Eb, A. J., *Virology* 54, pp. 536–539 (1973).

Alternatively, the reverting gene can be introduced into cells, in vitro or in vivo, via a transducing viral vector. See Tabin, C. J., Hoffmann, J. W., Goff, S. P., and Weinberg, R. A. (1982) "Adaption of a Retrovirus as a Eucaryotic Vector Transmitting the Herpes Simplex Virus Thymidine Kinase Gene", *Mol. Cel. Biol.* 2: 426–436. Use of retrovirus, for example, will infect a variety of cells and cause the antagonizing gene to be inserted into the genome of infected cells. Such infection could either be done with the aid of helper retrovirus, which would allow the virus to spread through the organism, or the antisense retrovirus could be produced in a helper-free system, such as $\psi$2-like cells (See Mann et al., *Cell*, 1983) that package amphotropic viruses. A helper-free virus might be employed to minimize spread throughout the organism. Viral vectors in addition to retroviruses can also be employed, such as paporaviruses, SV40-like viruses, or papilloma viruses.

The use of viruses to transfer genes into cells has recently been described in *Science*, 223, 1376, Mar. 30, 1984, and the teachings of this article are hereby incorporated by reference.

Vesicle fusion could also be employed to deliver the antagonizing gene. Vesicle fusion may be physically targeted to the tumor tissue if the vesicle were approximately designed to be taken up by the cells containing the oncogene. For example, vesicles containing asialoglycoproteins would be preferentially taken up by liver cells or other cells containing asialoglycoprotein receptor. Such a delivery system would be expected to have a lower efficiency of integration and expression of the antagonizing gene delivered, but would have a higher specificity than a retroviral vector. A combination strategy of targeted vesicles containing papilloma virus or retrovirus DNA molecules might provide a method for increasing the efficiency of expression of targeted molecules.

Still another alternative is to introduce the antagonizing gene via micro-injection. See for example, Laski et al., *Cell*, 1982.

The precise mechanisms of antagonism provided by introduction of an antagonizing gene are not well understood. It is clear, however, that the introduction of the antagonizing gene prevents the target oncogene from serving as a template for the synthesis of protein whose structure is translated from the RNA transcript of the oncogene. While not wishing to be bound by this explanation, it is possible that the antagonism stems from the ability of the anti-sense RNA transcript of the antagonizing gene to bond non-covalently to a sense RNA transcript of opposite polarity produced by transcription of the oncogene.

Figure 6:
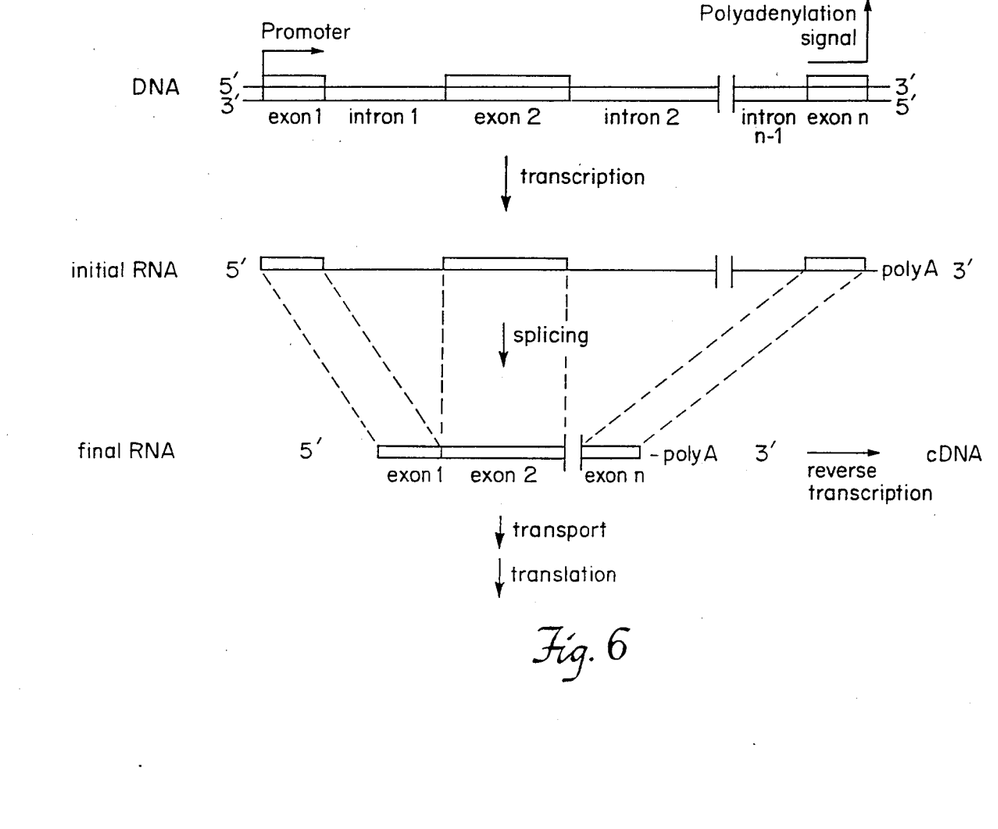
FIG. 6 is a schematic illustration of the treatment of double-stranded DNA containing a normal gene to produce an unspliced RNA transcript which is subsequently spliced.
Figure 7:
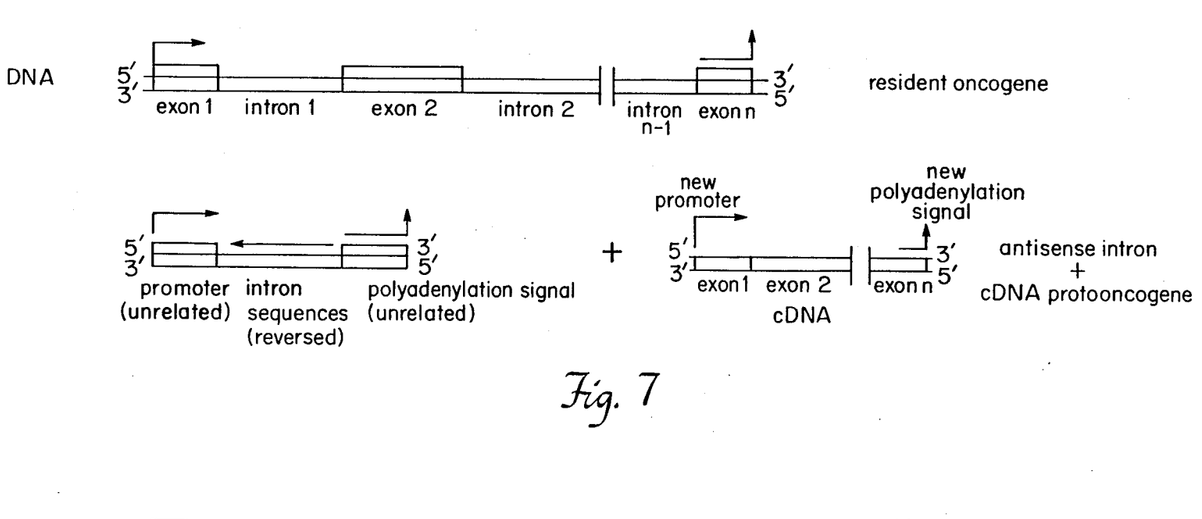
FIG. 7 is a schematic illustration of artificially-constructed genes for antagonizing oncogene function and restoring proto-oncogene function to a cell.
Figure 8:
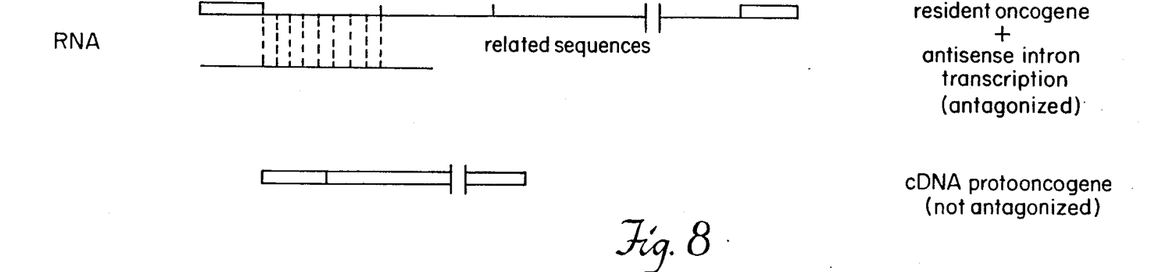
FIG. 8 is a schematic illustration of how the genes of FIG. 7 may operate.

The construction and functioning of two artificial genes, one of which is intended to antagonize oncogene function, and the other of which is intended to restore proto-oncogene function, will now be described with reference to FIGS. 6-8.

An antagonizing gene which will antagonize the function of a gene whose initial transcript is an unspliced RNA molecule is constructed. Such an antagonizing gene will not antagonize the function of a related gene whose initial transcript is already spliced. Thus, the antagonizing gene will be introduced into a tumor or transformed cell and antagonize the function of an unspliced oncogene residing in that cell. At the same time, a second gene is constructed and introduced into this cell. This second cointroduced gene is a cDNA constructed to express functions of the normal cellular counterpart of the oncogene and will therefore be termed a "proto-oncogene." Because this cointroduced proto-oncogene will express only an already spliced RNA transcript, its functioning will not be antagonized by the reverting gene. Consequently, by introducing the two genes into a tumor or transformed cell, oncogene function can be antagonized while simultaneously replacing proto-oncogene function.

The transcription of most cellular genes results in synthesis of RNA molecules having 2 types of RNA segments termed exons and introns. These exons and introns reside together in the same initial transcript. During subsequent maturation of the RNA molecule, the introns are removed in a process termed "splicing." The resulting spliced RNA molecule is then exported from its site of synthesis and maturation (the cellular nucleus) into its site of utilization (the cytoplasm). Artificial versions of the gene can be constructed that contain only those sequences of the gene which are represented in the spliced version of the gene. These artificial versions can be made, for example, by the reverse transcription of spliced RNA molecules, creating a complementary DNA copy of the spliced RNA molecule termed a cDNA copy.

The replacement method involves constructing a tripartite gene whose middle segment contains, in reverse orientation, an intron sequence which resides normally in the unspliced versions of the oncogene and related proto-oncogene. When this tripartite reverting gene is introduced into a tumor or transformed cell, it will antagonize function of the oncogene residing in that cell. A cointroduced gene carrying in normal orientation a cDNA version of the proto-oncogene will not be affected by the presence of the reverting gene, because this cDNA proto-oncogene does not carry the intron sequence whose transcription creates an RNA molecule that is antagonized by the reverting gene.

Figure 9:
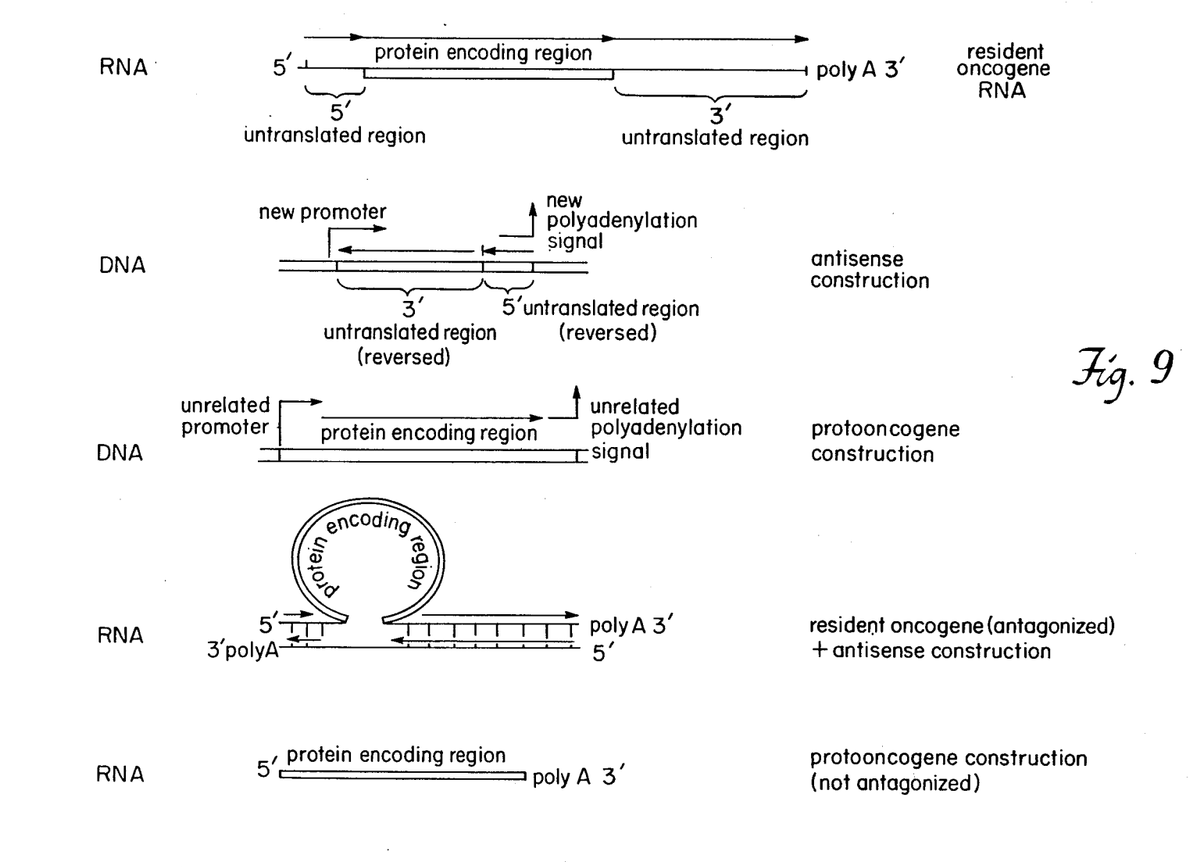
FIG. 9 is a schematic illustration of an alternate method for antagonizing oncogene function and restoring proto-oncogene function to a cell.

An alternative technique for antagonizing oncogene function and restoring proto-oncogene function to cells is illustrated in FIG. 9.

An antagonizing gene which will antagonize the functioning of an oncogene by generating anti-sense RNAs which are complementary to the untranslated portions of the messenger RNA of the oncogene is illustrated. This tripartite construction will serve as template for the synthesis of RNA segments that are complementary to (a) sequences of the oncogene mRNA which lie between the 5' (beginning) of the RNA and the site on the mRNA at which translation of the encoded oncogene protein is begun; or (b) sequences of the oncogene mRNA which lie between the 3' (end) of the protein-encoding portion of the mRNA at which translation is terminated and the 3' site of the mRNA at which polyadenylation is initiated; or (c) a combination of (a) and (b).

Into the same cell that acquires the above construction, a version of the normal proto-oncogene is introduced to serve as template for synthesis of a "sense" mRNA encoding a normal protein. This normal gene is constructed so that the mRNA synthesized on its DNA template will lack that portion or portions of the mRNA which are complementary to anti-sense RNAs that are synthesized on the reverting gene template. Thus, this normal construct will escape antagonism by the anti-sense RNAs.

Although the discussion herein, including the experimental work, has been directed to antagonizing oncogenes, it is believed that the methods of this invention can also be employed to antagonize the function of other functioning genes contained within the DNA of cells. Such genes might include, for example, genes responsible for such auto-immune diseases as arthritis, Huntington's Chorea, etc.

This invention will now be further and more specifically illustrated by the following example.

EXEMPLIFICATION

One $\mu$ g of pZIPNeo DNA (the 6-segment construct of FIG. 4) obtained from C. Cepko and R. Mulligan at the Massachusetts Institute of Technology was cut to completion with BamHI (New England Biolabs) and treated with calf intestinal phosphatase (Boehringer-Mannheim Biochemicals). The backbone plasmid pZIP is related to a plasmid described in *J. Virol.*, 44, 144–57, the teachings of which are incorporated by reference. The human c-Kirsten cDNA was isolated from an SV40-transformed human fibroblast library (see Okayama and Berg, *Mol. Cel. Biol.*, 3, p. 280, 1983). The 1.2 kb cDNA was isolated from the pcD vector by digestion with BamHI and subsequent gel purification. The cDNA and pZipNeo were ligated using T$_4$ DNA ligase (Collaborative Research) under standard conditions (50 mM Tris pH 7.6, 10 mM MgCl$_2$, 6.6 mM $\beta$-mercaptoethanol, 1 mM ATP). Recombinants were identified by restriction mapping.

PZipNeo, ZNCK (cDNA in sense orientation with respect to left LTR), and ZNKC (cDNA antisense orientation with respect to left LTR) were transfected by the method of Graham and van der Eb, *Virology* 52: 456 (1973) as modified by Anderson, Goldfarb and Weinberg, *Cell* 16: 63 (1979). Briefly, 50 ng of each DNA was mixed with 37.5 $\mu$g of sheared NIH3T3 carrier DNA, ethanol precipitated, and resuspended in 1.25 ml of 8 g/l NaCl, 5 g/l HEPES pH 6.95, and 0.15 g/l Na$_2$HPO$_4\times$7H$_2$O. To this was added with vortexing 50 $\mu$l of 2.5 M CaCl$_2$, and a precipitate was allowed to form for 30' at room temperature. SW-2-3 cells [McCoy et al., *Nature* 302: 79 (1983)] were fed with 5 mls of 10 percent calf serum/DME and the DNA precipitate. Four hours later the precipitate was removed and the cells refed with 10 mls of 10 percent calf serum/DME. Sixteen hours after transfection the cells were trypsinized and split 1 to 4. Twenty-four hours after transfection the cells were refed with medium containing 10 percent calf serum/DME/1 mg/ml G418 (Gibco). Cells were refed with this medium every three days. Sixteen days after transfection, G418-resistant colonies were picked using plexiglass cloning cylinders and grown up to make the cell lines described.

Cellular morphology was observed when the cells were at various stages of confluence in 10 cm dishes. Cells scored as transformed were refractile and splindly, and piled on top of each other. Cells scored as nontransformed were nonrefractile and strongly inhibited from overgrowing a monolayer. Of the ZipNeo lines, 4/5 scored transformed; of the ZNCK and 4/7 scored as transformed, and of the ZNKC lines, 5/6 scored as nontransformed.

Subsequently, ZNKC lines were analysed to insure that the transforming Kirsten-ras oncogene was still present. Total cellular DNA was isolated by lysis in 100 mM NaCl/10 mM Tris pH 7.6/10 mM EDTA/0.5% SDS and 0.2 $\mu$g/ml Prolinase K (Boehringer-Mannhein Biochemicals). Lysates were extracted twice with phenol, twice with chloroform, and ethanol precipitated. 10 $\mu$g of DNA were digested with XbaI (New England Biolabs) in 50 mM NaCl/10 mM Tris pH7.6/10 mM MgCl$_2$ and separated on a 1.1% agarose gel. DNA was transferred to nitrocellulose (Schliecher and Schuell) by the method of Southern [JMB 98:503 (1975)] and probed with $10^7$ cpm of human c-Kirsten-ras DNA nick translated to a specific activity of $6\times10^8$ cpm/$\mu$g. Hybridization was carried out in 50% formamide /S X SSCPE/1$\times$Denhardt's/100 $\mu$g/ml salmon sperm DNA at 42° for 16 hours. Filters were washed with 2$\times$SSCPE/0.1% SDS at 68° for 4 hours and exposed next to X-ray film overnight. The phenotypically nontransformed ZNKC lines were shown to contain two sets of Kirstein-ras sequences by this analysis: (1) the SW480-derived Kirsten-ras oncogene sequence; and (2) the transfected ZNKC sequence. Mouse c-Kirsten sequences should not hybridize at this stringency. This demonstrated that these cells were not transformed even though the oncogene segments were present.

In addition, cell lines were analysed for growth in soft agar, plating 10,000 cells into 0.35% nobel agar (Gibco) in 10% calf serum/DME and growing at 37° C. for two weeks. Phenotypically untransformed ZNKC lines showed up to 100-fold inhibition of colony-forming ability compared to parental SW-2-3 cells or Zip Neo-transfected cells.

Industrial Applicability

The invention described herein is useful in antagonizing transformation of cells caused by oncogenes within the cells, and in a particularly preferred embodiment, in restoring proto-oncogene function to the cells in addition to reversing the effects of the oncogene. In addition, treatment, in vivo, of other diseases, such as auto-immune diseases caused by malfunctioning genes can be treated by the methods of this invention. In addition, there are certain in vitro applications, such as antagonizing genes to prevent undesired gene products in commercially important products of cell lines. Such products might be proteases in a line used for purifying a protein, e.g., interferon or IL-2 producing lines, or gene products that contaminate otherwise pure preparations.

Equivalents

Those skilled in the art will recognize or be able to ascertain, using no more than routine experimentation, many equivalents to the specific embodiments of the invention described herein. Such equivalents are intended to be encompassed by the following claims.

We claim:

1. An artificially-contructed gene which, upon introduction into a cell containing an oncogene, antagonizes the function of said oncogene, said artificially-contructed gene containing the following DNA segments:
   a. a transcriptional promoter segment;
   b. a polyadenylation segment; and
   c. a segment of said oncogene, said oncongene segment located between said transcriptional promoter segment and said polyadenylation segment and being inverted with respect to said transcriptional promoter segment and said polyadenylation segment, the polarity of said inverted oncogene segment being the same as that of said transcriptional promoter segment and said polyadenylation segment, whereby transcription of the gene occurs in a direction opposite to the direction of transcription for the oncogene to thereby antagonize the function of said oncogene.

2. An artificially-constructed gene of claim 1 wherein said transcriptional promoter comprises a constitutive promoter segment.

3. An artificially-constructed gene of claim 1 wherein said transcriptional promoter comprises a regulatable promoter segment.

4. An artificially-constructed gene of claim 1 wherein said oncogene segment is derived from an isolated, naturally arising oncogene.

5. An artificially-constructed gene of claim 1 wherein said oncogene segment is derived from the protein-encoding portion of an oncogene.

6. An artificially-constructed gene of claim 1 wherein said oncogene segment is derived from a portion of an oncogene that does not encode protein structure.

7. An artificially-constructed gene of claim 1 wherein said oncogene segment is derived from portions of an oncogene that include protein-encoding portions and portions that encode other than proteins.

8. An artificially-constructed gene of claim 1 wherein said transcriptional promoter segment comprises a viral transcriptional promoter segment.

9. A method of antagonizing the effects of an oncogene in a cell, comprising:
   a. constructing a gene which, upon transcription in said cell, produces RNA transcript complementary to RNA transcript produced by said oncogene; and
   b. introducing said gene into the cell containing said oncogene.

10. A method of claim 9 wherein said gene contains a transcriptional promoter segment, a polyadenylation segment and an oncogene segment located between said transcriptional promoter segment and said polyadenylation segment and inverted with respect to transcriptional promoter segment and said polyadenylation segment, the polarity of said inverted oncogene segment being the same as that of said transcriptional promoter segment and said polyadenylation segment.

11. A method of claim 10 wherein said gene is introduced into said cell by transfection.

12. A method of claim 10 wherein said gene is introduced into said cell by a transducing viral vector.

13. A method of claim 12 wherein said viral vector comprises a retrovirus.

14. A method of claim 10 wherein said gene is introduced into said cell by microinjection.

15. A method of antagonizing the effect of an oncogene in a cell and restoring proto-oncogene function to said cell, comprising:
   a. constructing a first artificial gene which, upon transcription within said cell, produces an RNA transcript which antagonizes an unspliced RNA transcript involved in the function of said oncogene;
   b. constructing a second artificial gene which, upon transfection into said cell, produces a spliced RNA transcript which restores proto-oncogene function to said cell and whose function is not antagonized by said RNA transcript produced upon transcription of said first artificial gene in said cell; and
   c. introducing both of said first and said second artificial genes and into said cell whereby the effect of the oncogene is antagonized and the function of said proto-oncogene is restored.

16. A method of claim 15 wherein said first artificial gene contains intron sequences which reside normally in the unspliced version of the oncogene.

17. A method of claim 16 wherein said second artificial gene is constructed from cDNA produced from an RNA transcript from said proto-oncogene.

18. A method of antagonizing the effect of an oncogene in a cell and restoring proto-oncogene function to said cell, comprising:
   a. constructing a first artificial gene which, upon transcription in said cell, produces a first RNA transcript complementary to an untranslated portion of messenger RNA of said oncogene; and
   b. constructing a second artificial gene which, upon transcription in said cell, produces a second RNA transcript lacking untranslated portions which are complementary to sequences present in the first artificial gene, said second RNA transcript being sufficient to restore proto-oncogene function to said cell; and
   c. introducing said first and said second artificial genes into the cell containing said oncogene.

19. A method of claim 18 wherein said untranslated portions of the messenger RNA of the oncogene comprises sequences of the oncogene messenger RNA transcript lying between the 5' end of the RNA and the site on the RNA at which translation of the encoded oncogene protein is begun.

20. A method of claim 18 wherein said untranslated portions of the messenger RNA comprise sequences of the oncogene messenger RNA lying between the 3' end of the protein-encoding portion of the messenger RNA and the 3' site of the messenger RNA at which site polyadenylation is initiated.

21. A method of claim 18 wherein the untranslated portions of the messenger RNA are a combination of: (a) sequences of the oncogene messenger RNA transcript lying between the 5' end of the RNA and the site on the RNA at which translation of the encoded oncogene protein is begun and (b) sequences of the oncogene messenger RNA lying between the 3' end of the protein-encoding portion of the messenger RNA and the 3' site of the messenger RNA at which site polyadenylation is initiated.

22. A method of antagonizing the function of a gene in a cell, comprising:
   a. constructing an artificial gene which, upon transcription in said cell, produces RNA transcript complementary to RNA transcript produced by said gene; and
   b. introducing said artificially constructed gene into the cell containing said gene.

23. An artificially-constructed gene which, upon introduction into a cell containing an oncogene in conjuction with a gene which antagonizes the function of said oncogene, restores proto-oncogene function to said cell, comprising DNA which, upon transcription in said cell, results in production of spliced RNA.

24. An artificially-constructed gene of claim 24 in which the spliced RNA lacks intron DNA sequences.

25. A constructed gene which, upon introduction into a cell containing k-ras oncogene, antagonizes the function of said oncogene, said constructed gene containing the following DNA segments:
   a. a derivative of the pZIP clone of the Moloney murine leukemia provirus, said derivative being approximately 1 kb in size and comprising:
      (1) approximately 0.6 kb of the left LTR of Moloney murine leukemia provirus and
      (2) an additional segment which is the next region of the Moloney murine leukemia virus provirus, the region being approximately 0.4 kb in size and terminating at the first Pst I site normally present in the Moloney leukemia virus genome, the Pst I site being replaced by a BamHI endonuclease site, the derivative containing the transcriptional promoter of the virus;
   b. a derivative of the pZIP clone of the Moloney murine leukemia provirus, said derivative encompassing a splice-acceptor site of the provirus and originating from the provirus region defined by map units 5.9 to 6.3 and by the endonuclease sites BglIII and XbaI, the BglIII site having been modified to a BamHI endonuclease site and the XbaI site having been modified to an XhoI site;
   c. a 1.4 kb segment from the tn5 neomycin resistance gene of pBRneo, the segment having been inserted between HindIII and BamHI endonuclease sites at positions 29 and 375, respectively, within plasmid pBR322 and the two endonuclease sites having been replaced, respectively, by an XhoI endonuclease site and a null cleavage site;
   d. a 0.23 kb Simian virus 40 segment which includes the viral origin of replication and includes nucleotides 160 to 5154, inclusive, of the Simian virus 40 genome, the RII endonuclease site normally present at nucleotide 160 having been replaced by a null cleavage site and the HindIII endonuclease site normally present at nucleotide 5154 having been replaced by an EcoRI cleavage site;
   e. a 0.58 kb segment of plasmid pBR322 which contains the plasmid origin of replication and originates from a ThaI endonuclease-generated fragment which extends from nucleotide 2521 to nucleotide 3102, inclusive, of the pBR322 plasmid, the left ThaI endonuclease site having been replaced by an EcoRI endonuclease site and the right ThaI endonuclease site having been replaced by an XhoI endonuclease site;
   f. a 1.05 kb segment from the pZIP clone of the Moloney murine leukemia provirus, the segment of originating at a site 7.75 map units within the provirus and defined by HpaI endonuclease site present in the Moloney murine leukemia virus and including a segement approximately 0.45 kb in size, in which the right LTR of Moloney murine leukemia virus occurs, and an additional segment of the provirus, approximately 0.6 kb in size which extends beyond the right LTR, the HpaI endonuclease site having been replaced by an XhoI endonuclease site; and
   g. 1.2 kb DNA segment which is homologous to the human cKi-ras 2 gene, the 1.2 kb DNA segment present in the constructed gene at its BamHI endonuclease site and under the control of the transcriptional promoter of (a) such that the 1.2 kb DNA segment serves as template for synthesis of antisense RNA.

* * * * *

Notice of Adverse Decisions in Interference

In Interference No. 102,527, involving Patent No. 4,740,463, R. A. Weinberg, C. I. Bargmann, D. F. Stern, METHODS AND ARTIFICIAL GENES FOR ANTAGONIZING THE FUNCTION OF AN ONCOGENE, final judgment adverse to patentees was rendered Sept. 27, 1991, as to claims 1-25.
*(Official Gazette December 24, 1991).*